(12) United States Patent
Fukuda et al.

(10) Patent No.: US 7,514,571 B2
(45) Date of Patent: Apr. 7, 2009

(54) BICYCLO DERIVATIVE

(75) Inventors: Yasumichi Fukuda, Tochigi (JP);
Yoshikazu Asahina, Tochigi (JP);
Kazuya Yokota, Tochigi (JP); Koji Murakami, Tochigi (JP); Tomohiro Ide, Ibaraki (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/590,871

(22) PCT Filed: Feb. 22, 2005

(86) PCT No.: PCT/JP2005/002806
§ 371 (c)(1),
(2), (4) Date: Oct. 11, 2006

(87) PCT Pub. No.: WO2005/082847
PCT Pub. Date: Sep. 9, 2005

(65) Prior Publication Data
US 2007/0167501 A1    Jul. 19, 2007

(30) Foreign Application Priority Data
Feb. 27, 2004    (JP) ............... 2004-053305

(51) Int. Cl.
*A61K 31/40*    (2006.01)
*C07D 207/00*    (2006.01)

(52) U.S. Cl. ................... 548/540; 514/423

(58) Field of Classification Search ............ 548/540
See application file for complete search history.

(56) References Cited

U.S. PATENT DOCUMENTS

| | | | |
|---|---|---|---|
| 5,939,560 A | 8/1999 | Jenkins et al. | |
| 6,166,063 A | 12/2000 | Villhauer | |
| 6,201,132 B1 | 3/2001 | Jenkins et al. | |
| 6,432,969 B1 | 8/2002 | Villhauer | |
| 2001/0025023 A1 | 9/2001 | Carr | |
| 2001/0031780 A1 | 10/2001 | Kanstrup et al. | |
| 2002/0019411 A1 | 2/2002 | Robl et al. | |
| 2002/0103384 A1 | 8/2002 | Kanstrup et al. | |
| 2002/0193390 A1 | 12/2002 | Villhauer | |
| 2003/0100563 A1 | 5/2003 | Edmondson et al. | |
| 2003/0105077 A1 | 6/2003 | Kanstrup et al. | |
| 2003/0225102 A1 | 12/2003 | Sankaranarayanan | |
| 2004/0063935 A1 | 4/2004 | Yasuda et al. | |
| 2004/0072892 A1 | 4/2004 | Fukushima et al. | |
| 2004/0082607 A1 | 4/2004 | Oi et al. | |
| 2004/0106655 A1 | 6/2004 | Kitajima et al. | |
| 2004/0106802 A1 | 6/2004 | Sankaranarayanan | |
| 2004/0152745 A1 | 8/2004 | Jackson et al. | |
| 2004/0167133 A1 | 8/2004 | Edmondson et al. | |
| 2004/0167341 A1 | 8/2004 | Haffner et al. | |
| 2004/0171848 A1 | 9/2004 | Haffner et al. | |
| 2004/0176428 A1 | 9/2004 | Edmondson et al. | |
| 2004/0229926 A1 | 11/2004 | Yasuda et al. | |
| 2004/0242636 A1 | 12/2004 | Haffner et al. | |
| 2005/0054678 A1 | 3/2005 | Yasuda et al. | |
| 2005/0148606 A1 | 7/2005 | Kanstrup et al. | |
| 2005/0153973 A1 | 7/2005 | Aranyi et al. | |
| 2005/0176771 A1 | 8/2005 | Hayakawa et al. | |
| 2005/0245538 A1 | 11/2005 | Kitajima et al. | |
| 2006/0173056 A1 | 8/2006 | Kitajima et al. | |
| 2006/0241146 A1 | 10/2006 | Yasuda et al. | |
| 2006/0270679 A1 | 11/2006 | Edmondson et al. | |
| 2007/0112059 A1 | 5/2007 | Fukushima et al. | |
| 2007/0112205 A1 | 5/2007 | Fukushima et al. | |
| 2007/0265320 A1 | 11/2007 | Fukuda et al. | |

FOREIGN PATENT DOCUMENTS

| | | |
|---|---|---|
| JP | 2003-520849 | 7/2003 |
| JP | 2004-2367 | 1/2004 |
| JP | 2004-2368 | 1/2004 |
| JP | 2004-503531 | 2/2004 |
| WO | WO-98/19998 A2 * | 5/1998 |
| WO | 01/96295 | 12/2001 |
| WO | WO-03/002553 A2 * | 1/2003 |
| WO | 2004/007446 | 1/2004 |

OTHER PUBLICATIONS

Villhauer, CA 129:16059, 1998.*
U.S. Appl. No. 10/588,660.

* cited by examiner

*Primary Examiner*—Laura L. Stockton
(74) *Attorney, Agent, or Firm*—Wenderoth, Lind & Ponack, LLP.

(57) ABSTRACT

A novel bicyclo derivative represented by the following general formula (1), or a pharmaceutically acceptable salt thereof, acts as an effective DPP-IV inhibitor:

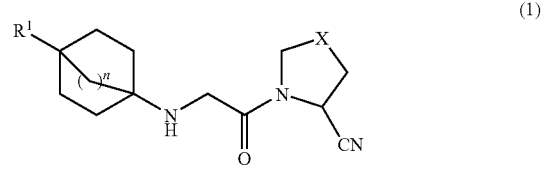

(1)

One example is (2S,4S)-1-[[N-(4-methylbicyclo[2,2,2]oct-1-yl)amino]acetyl]-4-fluoropyrrolidine-2-carbonitrile).

4 Claims, 1 Drawing Sheet

US 7,514,571 B2

BICYCLO DERIVATIVE

TECHNICAL FIELD

The present invention relates to bicyclo derivatives and pharmaceutically acceptable salts thereof that inhibit dipeptidylpeptidase IV (DPP-IV) and are useful in the prevention and/or treatment of type II diabetes and other diseases that involve DPP-IV.

BACKGROUND ART

Dipeptidylpeptidase IV (EC3,4,14,5, referred to as "DPP-IV" or "CD26," hereinafter) is a serine protease that specifically hydrolyzes polypeptides having proline or alanine at position 2 on the C-terminal side of these amino acid residues, cleaving dipeptides Xaa-Pro or Xaa-Ala from the N-terminus of the polypeptides (Xaa may be any amino acid).

One biological function of DPP-IV is the inactivation of glucagon-like peptide 1 (GLP-1) by cleaving the N-terminal His-Ala dipeptide of GLP-1 (Non-Patent Document 1). The GLP-1 inactivated by DPP-IV is thought to act as an antagonist on GLP-1 receptors, further decreasing the physiological activity of GLP-1 (Non-Patent Document 2). GLP-1, a peptide hormone secreted from endocrine L-cells found primarily in intestinal epithelium, is known to act on β-cells of the pancreatic Langerhans' islets in a glucose-dependent manner to promote the insulin secretion, thus decreasing the blood glucose level (Non-Patent Documents 3 and 4). Having an ability to promote insulin biosynthesis and β-cell growth, GLP-1 is an essential factor for the maintenance of β-cells (Non-Patent Documents 5 and 6). It has been reported that GLP-1 also acts to promote glucose utilization by peripheral tissue and, when intraventricularly administered, decreases food intake and motility of GI tract (Non-Patent Documents 7 through 10).

A DPP-IV inhibitor is believed to increase the GLP-1 activity by suppressing the decomposition of innate GLP-1. The increased GLP-1 activity stimulates insulin secretion and improves glucose metabolism. For this reason, DPP-IV inhibitors are expected to be useful in the prevention and/or treatment of diabetes, in particular type II diabetes (Non-Patent Documents 11 and 12). The compounds are expected to be also effective in the prevention and/or treatment of other diseases that are caused or worsened by decreased glucose metabolism (for example, diabetic complications, hyperinsulinemia, hyperglycemia, abnormal lipid metabolism and obesity).

The roles of DPP-IV in a living body other than the inactivation of GLP-1 and how the enzyme is involved in the onset of various diseases have been described in many reports as described below.

(a) DPP-IV inhibitors and their antibodies prevent the invasion of HIV into cells. Expression of CD26 is reduced in T-cells derived from patients infected with HIV-1 (Non-Patent Document 13). HIV-1 Tat protein binds to DPP-IV (Non-Patent Document 14).

(b) DPP-IV is involved in immune responses. DPP-IV inhibitors and their antibodies suppress the growth of T-cells stimulated by antigens (Non-Patent Document 15). T-cells stimulated by antigens express an increased level of DPP-IV (Non-Patent Document 16). DPP-IV is involved in the cytokine production and other functions of T-cells (Non-Patent Document 17). DPP-IV binds to adenosine deaminase (ADA) on the T-cell surface (Non-Patent Document 18).

(c) Expression of DPP-IV is increased in the skin fibroblasts of patients with rheumatoid arthritis, psoriasis, and lichen planus (Non-Patent Document 19).

(d) High DPP-IV activity is observed in patients with benign prostatic hypertrophy and in the homogenate of the prostatic tissue (Non-Patent Document 20). DPP-IV in the lung endothelium acts as an adhesive molecule for lung-metastatic breast cancer and prostatic cancer in rats (Non-Patent Document 21).

(e) The DPP-IV defective variant of F344 rats has lower blood pressure than the wild-type F344 rats. DPP-IV interacts with a protein that plays a crucial role in sodium reabsorption by the kidney (Patent Documents 1 and 2).

(f) The inhibition of DPP-IV activity offers an effective approach to the prevention and/or treatment of myelosuppressive diseases, while DPP-IV-activating agents are expected to serve as drugs to increase the white blood cell count and/or treat infectious diseases (Patent Document 3).

These observations indicate that DPP-IV inhibitors can be useful in the prevention and/or treatment of diabetes (in particular, type II diabetes) and/or diseases other than diabetic complications that involve DPP-IV. For example, DPP-IV inhibitors are expected to be useful in the prevention and/or treatment of AIDS following infection with HIV-1, rejection following organ/tissue transplantation, multiple sclerosis, rheumatoid arthritis, inflammation, allergies, osteoporosis, psoriasis and lichen planus, benign prostatic hypertrophy, lung metastasis of breast and prostatic cancers, hypertension and infectious diseases. DPP-IV inhibitors are also expected to be used to facilitate diuresis, decrease myelosuppression and increase white blood cell count.

Among existing DPP-IV inhibitors are pyrrolidine derivatives described in Patent Documents 4 through 11, heterocyclic derivatives described in Patent Documents 12 and 13, and β-amino acid derivatives described in Patent Documents 14 and 15.

Patent Document 16, a US patent, discloses a single bicycle [2,2,2]octane derivative that inhibits DPP-IV activity. This compound, however, is completely different from the compounds of the present invention in its structure and mechanism for DPP-IV inhibition. Patent Document 17 mentions a bicycle derivative structurally similar to the compounds of the present invention. However, there is no description in this literature concerning any of the compounds of the present invention, nor have any examples been presented of the compounds.

None of the previously described DPP-IV inhibitors are practical enough in terms of DPP-IV inhibitory activity, selectivity for DPP-IV, stability, toxicity and biological kinetics. Thus, a constant need exists for effective DPP-IV inhibitors.

[Non-Patent Document 1] American Journal of Physiology, Vol. 271 (1996): ppE458-E464.

[Non-Patent Document 2] European Journal of Pharmacology, Vol. 318 (1996): pp429-435

[Non-Patent Document 3]European Journal Clinical Investigation, Vol. 22 (1992): p154

[Non-Patent Document 4] Lancet, Vol. 2 (1987): p1300

[Non-Patent Document 5] Endocrinology, Vol. 42 (1992): p856

[Non-Patent Document 6] Diabetologia, Vol. 42 (1999):p 856

[Non-Patent Document 7] Endocrinology, Vol. 135 (1994): p2070

[Non-Patent Document 8] Diabetologia, Vol. 37 (1994): p1163

[Non-Patent Document 9] Digestion, Vol. 54 (1993): p392

[Non-Patent Document 10]Dig. Dis. Sci., Vol. 43 (1998): p1113
[Non-Patent Document 11]Diabetes, Vol. 47 (1998): pp1663-1670
[Non-Patent Document 12]Diabetologia, Vol. 42 (1999): pp1324-1331
[Non-Patent Document 13]Journal of Immunology, Vol. 149 (1992): p3073
[Non-Patent Document 14]Journal of Immunology, Vol. 150 (1993): p2544
[Non-Patent Document 15]Biological Chemistry (1991): p305
[Non-Patent Document 16]Scandinavian Journal of Immunology, Vol. 33 (1991): p737
[Non-Patent Document 17]Scandinavian Journal of Immunology, Vol. 29 (1989): p127
[Non-Patent Document 18]Science, Vol. 261 (1993): p466
[Non-Patent Document 19]Journal of Cellular Physiology, Vol. 151 (1992): p378
[Non-Patent Document 20]European Journal of Clinical Chemistry and Clinical Biochemistry, Vol. 30 (1992): p333
[Non-Patent Document 21]Journal of Cellular Physiology, Vol. 121 (1993): p1423
[Patent Document 1]WO 03/015775 Pamphlet
[Patent Document 2]WO 03/017936 Pamphlet
[Patent Document 3]WO 03/080633 Pamphlet
[Patent Document 4]WO 95/15309 Pamphlet
[Patent Document 5]WO 98/19998 Pamphlet
[Patent Document 6]WO 00/34241 Pamphlet
[Patent Document 7]WO 02/14271 Pamphlet
[Patent Document 8]WO 02/30890 Pamphlet
[Patent Document 9]WO 02/38541 Pamphlet
[Patent Document 10]WO 03/002553 Pamphlet
[Patent Document 11]US 02/0193390 Publication
[Patent Document 12]WO 02/062764 Pamphlet
[Patent Document 13]WO 03/004496 Pamphlet
[Patent Document 14]WO 03/000180 Pamphlet
[Patent Document 15]WO 03/004498 Pamphlet
[Patent Document 16]US 02/0193390 Publication
[Patent Document 17]WO 02/38541 Pamphlet

DISCLOSURE OF THE INVENTION

Problems to be Solved by the Invention

It is an object of the present invention to provide a novel compound that has high DPP-IV inhibitory activity, as well as pharmaceutically acceptable salts thereof. It is another object of the present invention to provide a pharmaceutical composition containing the novel compound that has high DPP-IV inhibitory activity or a pharmaceutically acceptable salt thereof. It is still another object of the present invention to provide a prophylactic and/or therapeutic agent for diabetes and associated complications, as well as a prophylactic and/or therapeutic agent for diseases involving DPP-IV.

Means to Solve the Problems

According to the present invention, there are provided a novel bicyclo derivative that has high DPP-IV inhibitory activity, and pharmaceutically acceptable salts thereof. Also provided is a pharmaceutical composition containing the novel bicyclo derivative that has high DPP-IV inhibitory activity, or a pharmaceutically acceptable salt thereof. Further provided are a prophylactic and/or therapeutic agent for diabetes and associated complications, and a prophylactic and/or therapeutic agent for diseases involving DPP-IV.

Thus, the present invention concerns a bicyclo derivative represented by the following general formula (1):

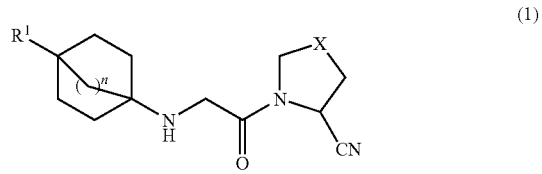

[wherein $R^1$ is a hydrogen atom, halogen atom, carboxyl group, $C_1$ to $C_4$ alkyl group which may be substituted with hydroxy group, or a substituted or unsubstituted aryl group; X is $CH_2$, CHF, $CF_2$, CHOH, S or O; and n is 1, 2 or 3], or a pharmaceutically acceptable salt thereof. The present invention also concerns pharmaceutical products and DPP-IV inhibitors that contain as an active ingredient the bicyclo derivative represented by the general formula (1) or a pharmaceutically acceptable salt thereof. The invention further concerns therapeutic agents that contain as an active ingredient the bicyclo derivative represented by the general formula (1) or a pharmaceutically acceptable salt thereof and are useful in the treatment of diseases involving DPP-IV, in particular diabetes and associated complications.

The term "$C_1$ to $C_4$ alkyl group" as used herein includes methyl group, ethyl group, propyl group, isopropyl group and t-butyl group. The term "substituted or unsubstituted aryl group" as used herein refers to aryl group that may have 1 to 5 substituents selected from halogen atom, C1 to C6 alkyl group, hydroxy group, C1 to C6 alkoxy group, C1 to C6 alkoxycarbonyl group, C1 to C6 alkylthio group, amino group, mono- or di-substituted C1 to C6 alkylamino group, 4- to 9-membered cyclic amino group that may contain 1 to 3 hetero atoms, formylamino group, C1 to C6 alkylcarbonylamino group, C1 to C6 alkoxycarbonylamino group, benzyloxycarbonylamino group, C1 to C6 alkylsulfonylamino group and substituted or unsubstituted arylsulfonylamino group.

The term "aryl group" as used herein refers to aromatic hydrocarbon or aromatic heterocyclic ring (such as 5- or 6-membered aromatic heteromonocyclic ring or 9- or 10-membered fused aromatic heterocyclic ring containing 1 to 3 hetero atoms selected from nitrogen atom, oxygen atom and sulfur atom), including benzene ring, naphthalene ring, anthracene ring, pyridine ring, pyrimidine ring, pyridazine ring, triazine ring, quinoline ring, naphthyridine ring, quinazoline ring, acridine ring, pyrrole ring, furan ring, thiophene ring, imidazole ring, pyrazole ring, oxazole ring, isoxazole ring, thiazole ring, indole ring, benzofuran ring, benzothiazole ring, benzimidazole ring and benzoxazole ring.

The term "halogen atom" as used herein refers to fluorine atom, chlorine atom, bromine atom and iodine atom.

Preferred examples of the compounds of the present invention include (2S,4S)-1-[[N-(4-carboxybicyclo[2,2,2]oct-1-yl)amino]acetyl]-4-fluoropyrrolidine-2-carbonitrile, (2S)-1-[[N-(4-carboxybicyclo[2,2,2]oct-1-yl)amino]acetyl]pyrrolidine-2-carbonitrile, (2S,4S)-1-[[N-(4-methylbicycle[2,2,2]oct-1-yl)amino]acetyl]-4-fluoropyrrolidine-2-carbonitrile, (2S)-1-[[N-(4-methylbicycle[2,2,2]oct-1-yl)amino]acetyl]pyrrolidine-2-carbonitrile, (2S,4S)-1-[[N-(4-hydroxymethylbicycle[2,2,2]oct-1-yl)amino]acetyl]-4-fluoropyrrolidine-2-carbonitrile, (2S)-1-[[N-(4-hydroxymethylbicycle[2,2,2]oct-1-yl)amino]acetyl]pyrrolidine-2-carbonitrile, (2S,4S)-1-[[N-(4-fluorobicyclo[2,2,2]oct-1-yl)amino]acetyl]-4-fluoropyrrolidine-2- carbonitrile, and (2S)-1-[[N-(4-fluorobicyclo[2,2,2]oct-1-yl) amino]acetyl]pyrrolidine-2-carbonitrile.

ADVANTAGE OF THE INVENTION

The compounds of the present invention include novel DPP-IV inhibitors that are useful not only in the prevention and/or treatment of diabetes and associated complications, but also in the prevention and/or treatment of other diseases involving DPP-IV.

BEST MODE FOR CARRYING OUT THE INVENTION

Figure 1:
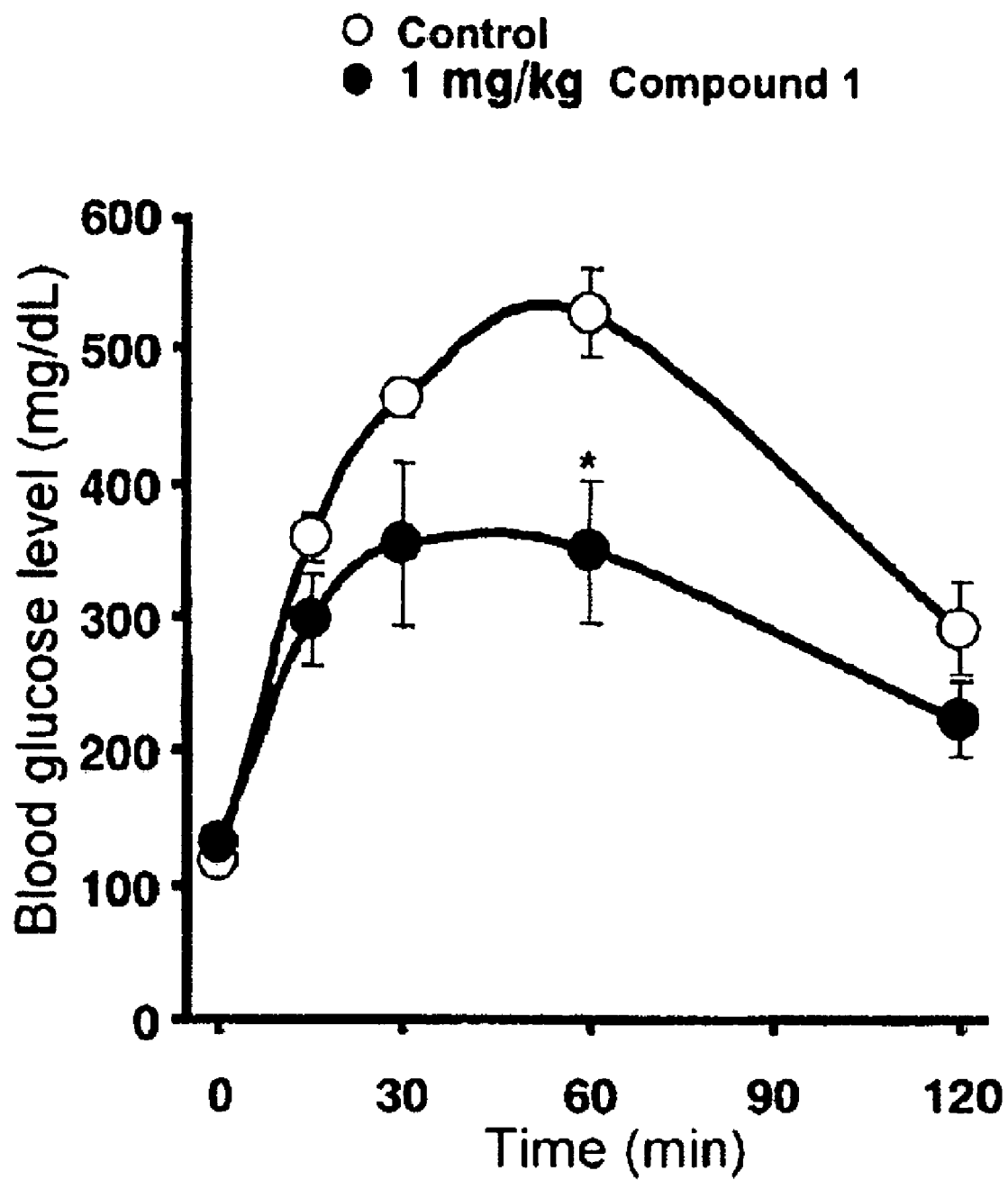
FIG. 1 is a graph showing the effect of Compound 1 on the plasma glucose level in normal mice, as determined in the oral glucose tolerance test. Each plot is given as the average of four examples ± standard deviation (T-test with P<0.05 vs control).

When the compounds of the present invention form pharmaceutically acceptable salts, they may form salts with inorganic acids, such as hydrochloric acid, hydrobromic acid, sulfuric acid, nitric acid and phosphoric acid; organic acids, such as acetic acid, maleic acid, fumaric acid, succinic acid, lactic acid, malic acid, tartaric acid, citric acid, methanesulfonic acid, p-toluenesulfonic acid, benzenesulfonic acid, salicylic acid, stearic acid, palmitic acid and trifluoroacetic acid; metals, such as sodium, potassium, calcium, magnesium, aluminum and zinc; ammoniums, such as ammonium and tetramethylammonium; organic amines, such as morpholine and piperidine; and amino acids, such as glycine, lysine, arginine, phenylalanine, and proline.

The compounds of the present invention represented by the general formula (1) or salts thereof may contain a single or two or more chiral centers and thus have multiple optical isomers resulting from these chiral centers. Any of these optical isomers and diastereomers are encompassed by the present invention, as are any mixtures thereof in an arbitrary mixing ratio, including racemic mixtures. When the compounds of the present invention represented by the general formula (1) or salts thereof contain a double bond, they may have Z- or E-configuration and any of the mixtures of these compounds in an arbitrary mixing ratio are also encompassed by the present invention. Some of the compounds of the present invention represented by the general formula (1) or salts thereof may have tautomers or rotational isomers, all of which isomers are encompassed by the present invention, as are any of the mixtures thereof in an arbitrary mixing ratio.

The compounds of the present invention represented by the general formula (1) or salts thereof include intramolecular salts, addition products, solvates, and hydrates thereof.

The compounds of the present invention represented by the general formula (1) or salts thereof may be used as a pharmaceutical composition either individually or in conjunction with one or more pharmaceutically acceptable auxiliary agents: They may be formulated with pharmaceutically acceptable carriers or excipients (such as starch, lactose, calcium phosphate, and calcium carbonate), lubricants (such as magnesium stearate, calcium stearate talc, and stearic acid), binders (such as starch, crystalline cellulose, carboxy methyl cellulose, gum arabic, polyvinyl pyrrolidone, and alginic acid), disintegrating agents (such as talc and carboxy methyl cellulose calcium) or diluents (such as saline, aqueous solutions of glucose, mannitol or lactose). Using ordinary techniques, the compounds of the present invention represented by the general formula (1) or salts thereof may be formulated into tablets, capsules, granules, powders, subtle granules, ampoules, or injections for oral or parenteral administration. The compounds of the present invention represented by the general formula (1) or salts thereof are generally administered to humans and other mammals at a dose of 0.0001 to 1000 mg/kg/day while the dose may vary depending on the type of the compound or salt, route of administration, and the age, body weight, and symptoms of the subjects. The compounds of the present invention or salts thereof may be administered in a single daily dose or multiple doses per day.

When necessary, the compounds of the present invention represented by the general formula (1) or salts thereof may be used in conjunction with one or more diabetic therapeutic agents other than DPP-IV inhibitors. Among such diabetic therapeutic agents for use with the compounds of the present invention or salts thereof are insulin and its derivatives, GLP-1 and its derivatives, and other oral diabetic therapeutic agents. Examples of the oral diabetic therapeutic agents include sulfonyl urea diabetic therapeutic agents, non-sulfonylurea insulin secretagogues, biguanide diabetic therapeutic agents, α-glycosidase inhibitors, glucagon antagonists, GLP-1 agonists, PPAR agonists, β3 agonists, SGLT inhibitors, PKC inhibitors, glucagon synthase kinase 3 (GSK-3) inhibitors, protein tyrosine phosphatase 1B (PTP-1B) inhibitors, potassium channel openers, insulin sensitizers, glucose uptake modulators, compounds modifying lipid metabolism, and appetite suppressors.

Examples of GLP-1 and its derivatives include betatropin and NN-2211. Examples of sulfonylurea diabetic therapeutic agents include tolbutamide, glibenclamide, gliclazide, glimepiride, and glipizide. Examples of non-sulfonylurea insulin secretagogues include nateglinide, repaglinide, mitiglinide, and JTT-608. Examples of biguanide diabetic therapeutic agents include metformin. Examples of α-glycosidase inhibitors include voglibose and miglitol. Examples of PPAR agonists include troglitazone, rosiglitazone, pioglitazone, ciglitizone, KRP-297 (MK-767), isaglitazone, GI-262570, and JTT-501. Examples of β3 agonists include AJ-9677, YM-178, and N-5984.

The compounds (1) of the present invention can be produced by various synthetic techniques. The compounds (1) of the present invention can be isolated or purified by common separation means (such as extraction, recrystallization, distillation, and chromatography). The compounds may be obtained in the form of various salts by using common techniques or similar techniques (such as neutralization).

Representative processes for producing the compounds of the present invention and salts thereof will now be described.

Process A

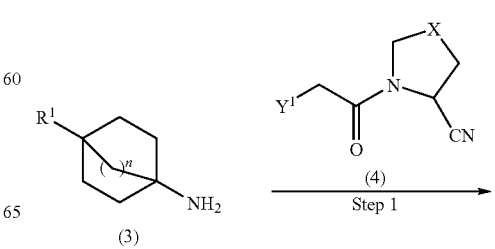

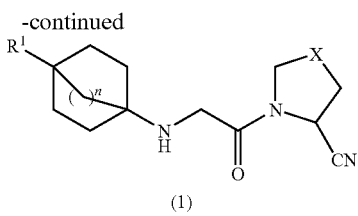

Step 1 (Process A)

In this step, a haloacetic acid derivative of the general formula (4) (where $Y^1$ is Cl or Br, and X is as defined above.) is reacted with a bicycloamine derivative of the general formula (3) (where $R^1$ and n are as defined above.) to obtain a bicyclo derivative of the general formula (1) (where $R^1$, n and X are as defined above.). The reaction is carried out in the presence or absence of a base. The base for use in this reaction may be an inorganic base, such as sodium hydroxide, potassium hydroxide, sodium bicarbonate, potassium bicarbonate, sodium carbonate, potassium carbonate and cesium carbonate, or an organic base, such as triethylamine, diisopropylethylamine, N,N,N,N-tetramethylethylenediamine, diazabicyclo[5.4.0]-7-undecene, diazabicyclo[4.3.0]-5-nonene, phosphazine base and pentaisopropylguanidine. When it is desired to use a catalyst in the reaction, such a catalyst may be a phase transfer catalyst or an inorganic salt, such as tetrabutylammonium bromide, tetrabutylammonium iodide, benzyltriethylammonium bromide, lithium bromide, lithium iodide, sodium iodide, potassium bromide, potassium iodide, cesium bromide and cesium iodide. The solvent for use in the reaction may be an inert solvent such as acetone, ethanol, toluene, acetonitrile, tetrahydrofuran, dioxane, ethylether, t-butylmethylether, dimethoxyethane, ethyl acetate, dichloromethane, N,N-dimethylformamide, dimethylsulfoxide and N-methyl-2-pyrrolidone. This reaction proceeds smoothly at 0 to 150° C.

Process B

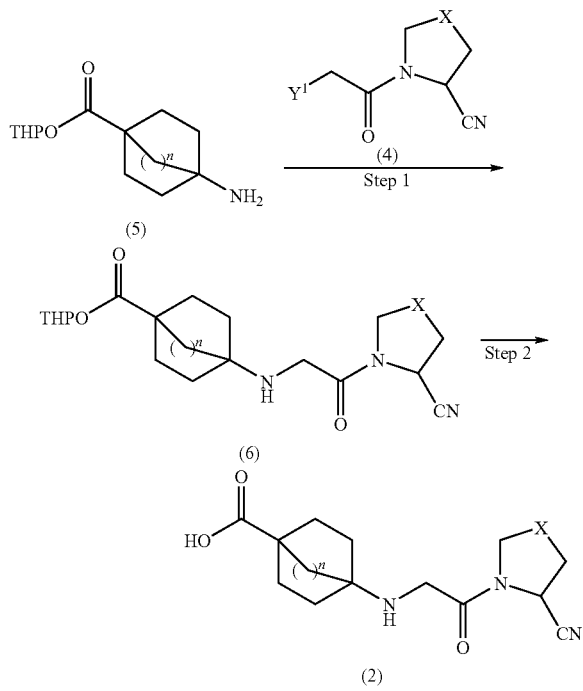

Step 1

Step 2

Step 1 (Process B)

In this step, a haloacetic acid derivative of the general formula (4) (where X and $Y^1$ are as described above) is reacted with a bicycloamine derivative of the general formula (5) (where n is as defined above and THP is tetrahydropyranyl group.) to obtain a bicyclo derivative of the general formula (6) (where n and X are as defined above.). The reaction is carried out in the presence or absence of a base. The base for use in this reaction may be an inorganic base, such as sodium hydroxide, potassium hydroxide, sodium bicarbonate, potassium bicarbonate, sodium carbonate, potassium carbonate and cesium carbonate, or an organic base, such as triethylamine, diisopropylethylamine, N,N,N,N-tetramethylethylenediamine, diazabicyclo[5.4.0]-7-undecene, diazabicyclo[4.3.0]-5-nonene, phosphazine base and pentaisopropylguanidine. When it is desired to use a catalyst in the reaction, the catalyst may be a phase transfer catalyst or an inorganic salt, such as tetrabutylammonium bromide, tetrabutylammonium iodide, benzyltriethylammonium bromide, lithium bromide, lithium iodide, sodium iodide, potassium bromide, potassium iodide, cesium bromide and cesium iodide. The solvent for use in the reaction may be an inert solvent such as acetone, ethanol, toluene, acetonitrile, tetrahydrofuran, dioxane, ethylether, t-butylmethylether, dimethoxyethane, ethyl acetate, dichloromethane, N,N-dimethylformamide, dimethylsulfoxide and N-methyl-2-pyrrolidone. This reaction proceeds smoothly at 0 to 150° C.

Step 2 (Process B)

In this step, the tetrahydropyranyl group of the bicyclo derivative of the general formula (6) (where n and X are as defined above.) is removed to obtain a bicyclo derivative of the general formula (2) (where n and X are as defined above.). Tetrahydropyranyl group can be readily removed by using acetic acid, p-toluenesulfonic acid or hydrochloric acid according to a known technique.

The advantageous features of the present invention will now be described with reference to Test Examples and Examples, which are not intended to limit the scope of the invention in any way.

REFERENCE EXAMPLE 1

Synthesis of 2-tetrahydropyranyl 4-aminobicyclo[2,2,2]octane-1-carboxylate

Step 1:

Synthesis of methyl 4-benzyloxycarbonylaminobicyclo[2,2,2]octane-1-carboxylate

Methyl hydrogen bicyclo[2,2,2]octane-1,4-dicarboxylate (25.0 g), diphenylphosphoryl azide (32.5 g), triethylamine (17.3 mL) and toluene (500 mL) were mixed together. The mixture was stirred for 2 hours at room temperature and was refluxed for 2 hours. To the resulting mixture, benzylalcohol (122 mL) was added and the mixture was further refluxed for 17 hours. Subsequently, the mixture was allowed to cool and was sequentially washed with a 10% aqueous citric acid, saturated aqueous solution of sodium bicarbonate and saturated brine. The mixture was then dried over anhydrous sodium sulfate and concentrated under reduced pressure. The residue was purified by silica gel column chromatography (eluant: hexane: ethyl acetate=2:1) to give methyl 4-benzyloxycarbonylaminobicyclo[2,2,2]octane-1-carboxylate (32.2 g).

MS (FAB$^+$) m/z: 318 (MH$^+$)

Step 2:

Synthesis of 4-benzyloxycarbonylaminobicyclo[2,2,2]octane-1-carboxylic acid

Methyl 4-benzyloxycarbonylaminobicyclo[2,2,2]octane-1-carboxylate (64.3 g) was dissolved in ethanol (1100 mL). To this solution, a 1 mol/L aqueous solution of sodium hydroxide (1000 mL) was added and the mixture was stirred at 50° C. for 1 hour. Ethanol in the mixture was evaporated under reduced pressure and the residue was washed with diethylether (500 mL), followed by addition of concentrated hydrochloric acid to adjust the pH to 1. The resulting crystals were filtrated, washed with water, dried under reduced pressure to give 4-benzyloxycarbonylaminobicyclo[2,2,2]octane-1-carboxylic acid (56.1 g).

MS (FAB$^+$) m/z: 304 (MH$^+$)

Step 3:

Synthesis of 2-tetrahydropyranyl 4-benzyloxycarbonylaminobicyclo[2,2,2]octane-1-carboxylate 4-Benzyloxycarbonylaminobicyclo[2,2,2]octane-1-carboxylic acid (1.00 g) was suspended in dichloromethane (10 mL). To this suspension, 3,4-dihydro-2H-pyran (1.20 mL) and then p-toluenesulfonic acid monohydrate (6.3 mg) were added and the mixture was stirred at room temperature for 30 minutes. Subsequently, the reaction mixture was sequentially washed with a saturated aqueous sodium bicarbonate solution and water, dried over anhydrous sodium sulfate and concentrated under reduced pressure. The residue was purified by silica gel column chromatography (eluant: hexane: ethyl acetate=4:1) to give 2-tetrahydropyranyl 4-benzyloxycarbonylaminobicyclo[2,2,2]octane-1-carboxylate (1.18 g).

$^1$H NMR (CDCl$_3$) δ 1.53-1.95 (m, 18H), 3.67-3.71 (m, 1H), 3.82-3.89 (m, 1H), 4.59 (br, 1H), 5.03 (s, 2H), 5.95 (br, 1H), 7.29-7.38 (m, 5H).

Step 4:

Synthesis of 2-tetrahydropyranyl 4-aminobicyclo[2,2,2]octane-1-carboxylate

Using 2-tetrahydropyranyl 4-benzyloxycarbonylaminobicyclo[2,2,2]octane-1-carboxylate (548 mg), the same procedure was followed as in Step 4 of Reference Example 1 to give 2-tetrahydropyranyl 4-aminobicyclo[2,2,2]octane-1-carboxylate (357 mg).

MS (EI$^+$) m/z: 253 (M$^+$)

REFERENCE EXAMPLE 2

Synthesis of 4-amino-1-hydroxymethylbicyclo[2,2,2]octane

Step 1:

Synthesis of 4-benzyloxycarbonylamino-1-hydroxymethylbicyclo[2,2,2]octane

4-Benzyloxycarbonylaminobicyclo[2,2,2]octane-1-carboxylic acid (500 mg) was dissolved in tetrahydrofuran (8 mL). While the solution was chilled in a salt/ice bath, N-methylmorpholine (0.18 mL) was added. This was followed by dropwise addition of ethyl chlorocarbonate (0.16 mL) and stirring for 10 minutes. To the reaction mixture, sodium borohydride (187 mg) and then methanol (15 mL) were added and the mixture was stirred below 0° C. for 1 hour. Subsequently, the reaction mixture was concentrated under reduced pressure. To the resulting residue, water was added and the solution was extracted with ethyl acetate. The ethyl acetate layer was then washed sequentially with 1 mol/L hydrochloric acid and water, was dried over anhydrous sodium sulfate, and was concentrated under reduced pressure. The residue was purified by silica gel chromatography (eluant: hexane: ethyl acetate=1:1) to obtain 4-benzyloxycarbonylamino-1-hydroxymethylbicyclo[2,2,2]octane (453 mg).

MS (EI$^+$) m/z: 289 (M$^+$)

Step 2:

Synthesis of 4-amino-1-hydroxymethylbicyclo[2,2,2]octane

Using 4-benzyloxycarbonylamino-1-hydroxymethylbicyclo[2,2,2]octane (448 mg), the same procedure was followed as in Step 4 of Reference Example 1 to obtain 4-amino-1-hydroxymethylbicyclo[2,2,2]octane (185 mg).

MS (EI$^+$) m/z: 155 (M$^+$).

REFERENCE EXAMPLE 3

Synthesis of 1-amino-4-fluorobicyclo[2,2,2]octane

Step 1

Synthesis of 1-benzyloxycarbonylamino-4-fluorobicyclo[2,2,2]octane

Using 4-fluorobicyclo[2,2,2]octane-1-carboxylic acid (265 mg), the same procedure was followed as in Step 1 of Reference Example 1 to obtain 1-benzyloxycarbonylamino-4-fluorobicyclo[2,2,2]octane (365 mg).

MS (EI$^+$) m/z: 277 (M$^+$)

Step 2:

Synthesis of 1-amino-4-fluorobicyclo[2,2,2]octane

Using 1-benzyloxycarbonylamino-4-fluorobicyclo[2,2,2]octane (350 mg), the same procedure was followed as in Step 4 of Reference Example 1 to obtain 1-amino-4-fluorobicyclo[2,2,2]octane (144 mg).

MS (EI$^+$) m/z: 143 (M$^+$).

REFERENCE EXAMPLE 4

Synthesis of (2S,4S)-1-(2-chloroacetyl)-4-fluoropyrrolidine-2-carbonitrile

According to the process for producing (2S,4S)-1-(2-bromoacetyl)-4-fluoropyrrolidine-2-carbonitrile described in WO02/38541 pamphlet, (2S,4S)-4-fluoropyrrolidine-2-carboxamide hydrochloride (5.00 g) and chloroacetylchloride (2.60 mL) were used to obtain (2S,4S)-1-(2-chloroacetyl)-4-fluoropyrrolidine-2-carbonitrile (4.96 g).

MS (EI$^+$) m/z: 190 (M$^+$).

HRMS (EI$^+$) for C$_7$H$_8$ClFN$_2$O(M$^+$): calcd, 190.0309; found, 190.0283.

EXAMPLE 1

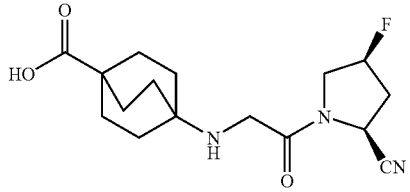

Synthesis of (2S,4S)-1-[[N-(4-carboxybicyclo[2,2,2]oct-1-yl)amino]acetyl]-4-fluoropyrrolidine-2-carbonitrile Step 1:

Synthesis of (2S,4S)-1-[[N-[4-(2-tetrahydropyranyl)oxycarbonylbicyclo[2,2,2]oct-1-yl]amino]acetyl]-4-fluoropyrrolidine-2-carbonitrile 2-Tetrahydropyranyl 4-aminobicyclo[2,2,2]octane-1-carboxylate (62.9 mg) was suspended in acetonitrile (1 mL). To this suspension, diisopropylethylamine (47 μL) was added. With the solution chilled in an ice bath, (2S,4S)-1-(2-bromoacetyl)-4-fluoropyrrolidine-2-carbonitrile (53.1 mg) in acetonitrile (0.8 mL) was added and the mixture was stirred for 4 hours. Subsequently, the reaction mixture was concentrated, and ethyl acetate and water were added to dissolve the residue. To this solution, an aqueous sodium bicarbonate solution was added to make the solution basic and the solution was extracted with ethyl acetate. The ethyl acetate layer was washed with saturated brine, dried over anhydrous sodium sulfate, and concentrated under reduced pressure. The resulting residue was purified by silica gel column chromatography (eluant: dichloromethane: methanol=10:1) to obtain (2S,4S)-1-[[N-[4-(2-tetrahydropyranyl)oxycarbonylbicyclo[2,2,2]oct-1-yl]amino]acetyl]-4-fluoropyrrolidine-2-carbonitrile (73.3 mg).

MS (FAB$^+$) m/z: 408 (MH$^+$).

HRMS (FAB$^+$) for $C_{21}H_{31}FN_3O_4$ (MH$^+$): calcd, 408.2299; found, 408.2295.

Step 2:

Synthesis of (2S,4S)-1-[[N-(4-carboxybicyclo[2,2,2]oct-1-yl)amino]acetyl]-4-fluoropyrrolidine-2-carbonitrile (2S,4S)-1-[[N-[4-(2-Tetrahydropyranyl)oxycarbonylbicyclo[2,2,2]oct-1-yl]amino]acetyl]-4-fluoropyrrolidine-2-carbonitrile (71.6 mg) was dissolved in acetic acid (4 mL) and the solution was stirred at room temperature for 6 hours. Subsequently, the reaction mixture was concentrated under reduced pressure and the residue was suspended in dichloromethane and was collected by filtration. This gave (2S,4S)-1-[[N-(4-carboxybicyclo[2,2,2]oct-1-yl)amino]acetyl]-4-fluoropyrrolidine-2-carbonitrile (31.4 mg).

MS (EI$^+$) m/z: 323 (M$^+$).

EXAMPLE 2

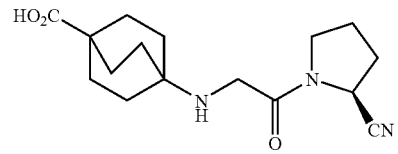

Synthesis of (2S)-1-[[N-(4-carboxybicyclo[2,2,2]oct-1-yl)amino]acetyl]pyrrolidine-2-carbonitrile Step 1:

Synthesis of (2S)-1-[[N-[4-(2-tetrahydropyranyl)oxycarbonylbicyclo[2,2,2]oct-1-yl]amino]acetyl]pyrrolidine-2-carbonitrile Using 2-tetrahydropyranyl 4-aminobicyclo[2,2,2]octane-1-carboxylate (90.0 mg) and (2S)-1-(2-bromoacetyl)pyrrolidine-2-carbonitrile (70.0 mg), the same procedure was followed as in Example 1 to obtain (2S)-1-[[N-[4-(2-tetrahydropyranyl)oxycarbonylbicyclo[2,2,2]oct-1-yl]amino]acetyl]pyrrolidine-2-carbonitrile (85.2 mg).

MS (EI$^+$) m/z: 383 (M$^+$).

HRMS (EI$^+$) for $C_{21}H_{31}N_3O_4$ (M$^+$): calcd, 383.2315; found, 383.2296.

Step 2:

Synthesis of (2S)-1-[[N-(4-carboxybicyclo[2,2,2]oct-1-yl)amino]acetyl]pyrrolidine-2-carbonitrile Using (2S)-1-[[N-[4-(2-tetrahydropyranyl)oxycarbonylbicyclo[2,2,2]oct-1-yl]amino]acetyl]pyrrolidine-2-carbonitrile (73.0 mg), the same procedure was followed as in Example 1 to obtain (2S)-1-[[N-[4-carboxybicyclo[2,2,2]oct-1-yl]amino]acetyl]pyrrolidine-2-carbonitrile (56.0 mg).

MS (EI$^+$) m/z: 305 (M$^+$).

HRMS (EI$^+$) for $C_{16}H_{23}N_3O_3$ (M$^+$): calcd, 305.1739; found, 305.1736.

EXAMPLE 3

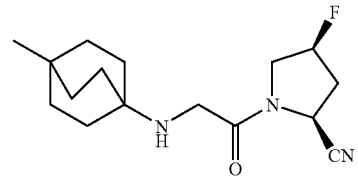

Synthesis of (2S,4S)-1-[[N-(4-methylbicyclo[2,2,2]oct-1-yl)amino]acetyl]-4-fluoropyrrolidine-2-carbonitrile Using 4-amino-1-methylbicyclo[2,2,2]octane (56.0 mg) and (2S,4S)-1-(2-bromoacetyl)-4-fluoropyrrolidine-2-carbonitrile (95.0 mg), the same procedure was followed as in Example 1 to obtain (2S,4S)-1-[[N-(4-methylbicyclo[2,2,2]oct-1-yl)amino]acetyl]-4-fluoropyrrolidine-2-carbonitrile (89.2 mg).

MS (EI$^+$) m/z: 293 (M$^+$).

HRMS (EI$^+$) for $C_{16}H_{24}FN_3O$ (M$^+$): calcd, 293.1903; found, 293.1881.

EXAMPLE 4

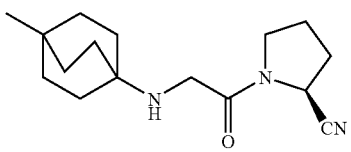

Synthesis of (2S)-1-[[N-(4-methylbicyclo[2,2,2]oct-1-yl)amino]acetyl]pyrrolidine-2-carbonitrile Using 4-amino-1-methylbicyclo[2,2,2]octane (75.0 mg) and (2S)-1-(2-bromoacetyl)pyrrolidine-2-carbonitrile (110 mg), the same procedure was followed as in Example 1 to obtain (2S)-1-[[N-(4-methylbicyclo[2,2,2]oct-1-yl)amino]acetyl]pyrrolidine-2-carbonitrile (84.0 mg).

MS (EI$^+$) m/z: 275 (M$^+$).
HRMS (EI$^+$) for $C_{16}H_{25}N_3O$ (M$^+$): calcd, 275.1998; found, 275.1981.

EXAMPLE 5

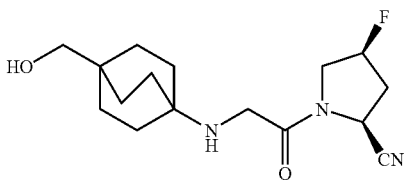

Synthesis of (2S,4S)-1-[[N-(4-hydroxymethylbicyclo[2,2,2]oct-1-yl)amino]acetyl]-4-fluoropyrrolidine-2-carbonitrile Using 4-amino-1-hydroxymethylbicyclo[2,2,2]octane (50.0 mg) and (2S,4S)-1-(2-bromoacetyl)-4-fluoropyrrolidine-2-carbonitrile (75.7 mg), the same procedure was followed as in Example 5 to obtain (2S,4S)-1-[[N-(4-hydroxymethylbicyclo[2,2,2]oct-1-yl)amino]acetyl]-4-fluoropyrrolidine-2-carbonitrile (93.0 mg).

MS (FAB$^+$) m/z: 310 (MH$^+$).
HRMS (FAB$^+$) for $C_{16}H_{25}FN_3O_2$ (MH$^+$): calcd, 310.1931; found, 310.1942.

EXAMPLE 6

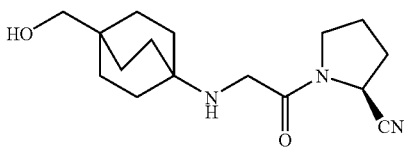

Synthesis of (2S)-1-[[N-(4-hydroxymethylbicyclo[2,2,2]oct-1-yl)amino]acetyl]pyrrolidine-2-carbonitrile Using 4-amino-1-hydroxymethylbicyclo[2,2,2]octane (50.5 mg) and (2S)-1-(2-bromoacetyl)pyrrolidine-2-carbonitrile (61.7 mg), the same procedure was followed as in Example 5 to obtain (2S)-1-[[N-(4-hydroxymethylbicyclo[2,2,2]oct-1-yl)amino]acetyl]pyrrolidine-2-carbonitrile (57.0 mg).

MS (FAB$^+$) m/z: 292 (MH$^+$)
HRMS (FAB$^+$) for $C_{16}H_{25}N_3O_2$ (MH$^+$) calcd, 292.2025; found, 292.2025.

EXAMPLE 7

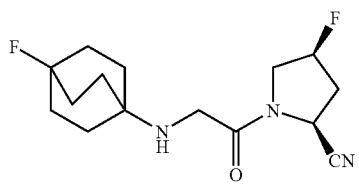

Synthesis of (2S,4S)-1-[[N-(4-fluorobicyclo[2,2,2]oct-1-yl)amino]acetyl]-4-fluoropyrrolidine-2-carbonitrile Using 4-amino-1-fluorobicyclo[2,2,2]octane (50.0 mg) and (2S,4S)-1-(2-bromoacetyl)-4-fluoropyrrolidine-2-carbonitrile (82.1 mg), the same procedure was followed as in Example 10 to obtain (2S,4S)-1-[[N-(4-fluorobicyclo[2,2,2]oct-1-yl)amino]acetyl]-4-fluoropyrrolidine-2-carbonitrile (93.1 mg).

MS (EI$^+$) m/z: 297 (M$^+$).
HRMS (EI$^+$) for $C_{15}H_{21}F_2N_3O$ (M$^+$): calcd, 297.1653; found, 297.1628.

EXAMPLE 8

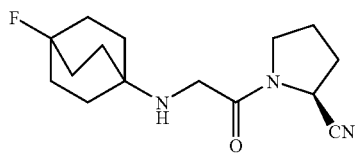

Synthesis of (2S)-1-[[N-(4-fluorobicyclo[2,2,2]oct-1-yl)amino]acetyl]pyrrolidine-2-carbonitrile Using 4-amino-1-fluorobicyclo[2,2,2]octane (50.0 mg) and (2S)-1-(2-bromoacetyl)pyrrolidine-2-carbonitrile (73.5 mg), the same procedure was followed as in Example 10 to obtain (2S)-1-[[N-(4-fluorobicyclo[2,2,2]oct-1-yl)amino]acetyl]pyrrolidine-2-carbonitrile (72.3 mg).

MS (EI$^+$) m/z: 279 (M$^+$).
HRMS (EI$^+$) for $C_{15}H_{22}FN_3O$ (M$^+$): calcd, 279.1747; found, 279.1766.

TEST EXAMPLE 1

Test for the Ability of the Compounds of the Invention to Inhibit of Dipeptidylpeptidase IV Activity The concentration of free 7-amino-4-methyl-coumarin (AMC) generated by hydrolysis of H-Gly-Pro-AMC.HBr substrate by plasma dipeptidylpeptidase IV was determined by fluorometry.

Method

A 20 μL of buffer (25 mmol/L hepes, 140 mmol/L sodium chloride, 1% bovine serum albumin, 80 mmol/L magnesium chloride hexahydrate, pH 7.4) containing each compound was added to 20 μL of plasma diluted 8-fold with saline in a well of a 96-well flat bottom plate. The plate was left at room temperature for 5 minutes and 10 μL of 0.1 mmol/L H-Gly-Pro-AMC.HBr solution was added to each well to initiate the reaction. The plate was left in a dark environment at room temperature for 20 minutes, at which point 20 μL 25% acetic acid was added to terminate the reaction. Using a fluorescent plate reader, the free AMC concentration was determined by exciting the samples at 355 nm and measuring the fluorescence intensity at 460 nm. Using Prism 3.02 (GraphPad Software), the results were analyzed to determine the 50% inhibitory concentration (IC50). The results are shown in Table 1.

TABLE 1

| In vitro dipeptidylpeptidase IV inhibition | |
|---|---|
| Test compound | IC50 (nmol/L) |
| Example 1 | 3.1 |
| Example 3 | 0.25 |
| Example 5 | 1.1 |
| Compound A | 3.3 |

Compound A: (2S)-1-[[(3-hydroxy-1-adamantyl)amino]acetyl]-2-cyanopyrrolidine (LAF-237)

TEST EXAMPLE 2

Test for the Inhibition of Dipeptidylpeptidase IV Activity in mice by Oral Administration of the Compounds of the Invention Each compound was suspended in 0.3% sodium carboxymethylcellulose to a concentration of 0.1 mg/mL. The preparation was orally administered to 8 weeks old male ICR mice (Charles River Laboratories Japan) at a dose of 10 mL/kg. Using an EDTA 2K-treated capillary tube, blood samples were collected from the tail vein before administration and 30 minutes after administration. The blood samples were centrifuged at 6000 rpm for 2 minutes to separate plasma. The enzymatic activity was determined using the same procedure as in Test Example 1. The inhibition was determined from the decrease in the enzymatic activity from the initial activity (% inhibition={(activity before administration−activity after administration)/(activity before administration)}×100). The results are shown in Table 2.

TABLE 2

| Inhibition of plasma dipeptidylpeptidase IV activity in mice by oral administration | |
|---|---|
| Test compound | % inhibition |
| Example 3 | 100 |
| Example 7 | 91 |
| Compound A | 81 |

Compound A: (2S)-1-[[(3-hydroxy-1-adamantyl)amino]acetyl]-2-cyanopyrrolidine (LAF-237)

TEST EXAMPLE 3

Oral Glucose tolerance Test in Mice

The compound of the present invention of Example 5 was suspended in 0.3% sodium carboxymethylcellulose (CMC-Na, Sigma). Seven weeks old male ICR mice (Charles River Laboratories Japan) were acclimatized for a week. During the acclimatization period, the animals were allowed to freely consume standard feed (CE-2, Clea Japan) and water. Starting from week 8, the ICR mice were fasted for 16 hours. Subsequently, mice were orally administered 0.3% CMC-Na (10 mL/kg) or Compound 1 (1 mg/kg, 10 mL/kg). 30 minutes after the administration, a glucose solution was orally administered at a dose of 5 g/kg. Using an EDTA 2K-treated capillary tube, blood samples were collected from the tail vein before administration of glucose solution and 15, 30, 60, and 120 minutes after administration. The blood glucose level was determined using glucose B-test Wako (Wako Pure Chemical Industries). The results were shown in means ± standard errors. Statistical analysis was performed using t-test with a significant level of less than 5%. The results are shown in FIG. 1.

TEST EXAMPLE 4

Test for the Efficacy of the Compounds of the Invention Against Drug-induced Hypoleukocytosis The efficacy of the compounds of the present invention against drug-induced hypoleukocytosis was evaluated by conducting an experiment according to the method described by Okabe et al (Japanese Pharmacology and Therapeutics, Vol. 19, No. 6 (1991): p55).

Eight weeks old male ICR mice (Charles River Laboratories Japan) were intraperitoneally administered a single dose of cyclophosphamide (200 mg/kg) on Day 0. Starting from the following day, control group was given saline and test group was orally administered the compound of the present invention (1 to 200 mg/kg) once or twice a day over a five day period. Blood samples were collected 2, 4, 6, and 8 days after the beginning of the test and the white blood cell count was monitored over time. The white blood cell count of the test group at a given time was compared with the white blood cell count before administration of cyclophosphamide to evaluate the efficacy of the compound of the present invention against the drug-induced hypoleukocytosis. The results indicate that the decrease in the white blood cell count is significantly suppressed in the group administered the compound of the present invention as compared to control group.

TEST EXAMPLE 5

Test for the Ability of the Compounds of the Invention to Increase the Blood G-CSF Level Seven weeks old male ICR mice (Charles River Laboratories Japan) were used. Control group was given saline and test group was orally administered the compound of the present invention (1 to 200 mg/kg) once or twice a day over a five day period. Mice were anesthetized on the day following the cessation of administration and blood samples were collected. Plasma G-CSF level was determined using mouse G-CSF ELISA kit (R&D SYSTEM). The results indicate that the plasma G-CSF level was significantly increased in the group administered the compound of the present invention as compared to control group.

INDUSTRIAL APPLICABILITY

As set forth, the compounds of the present invention are novel bicyclo derivatives and pharmaceutically acceptable salts thereof that effectively inhibit DPP-IV. Pharmaceutical compositions that contain the present compound as an active ingredient are useful in the prevention and/or treatment of diabetes and associated diabetic complications, as well as in the prevention and/or treatment of other diseases that involve DPP-IV.

What is claimed is:

1. A bicyclo derivative represented by the following general formula (1):

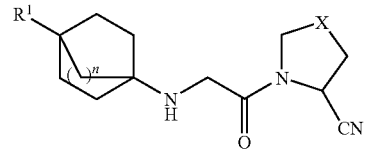

wherein $R^1$ is a carboxyl group; X is $CH_2$, CHF, $CF_2$, or CHOH; and n is an integer of 1 to 3, or a pharmaceutically acceptable salt thereof.

2. A pharmaceutical composition containing as an active ingredient the bicyclo derivative of claim 1 or a pharmaceutically acceptable salt thereof, and a pharmaceutically acceptable auxiliary agent.

3. A method for treating a mammal having a disease involving DPP-IV, wherein the disease is diabetes which comprises administering a therapeutically effective amount of the bicyclo derivative of claim 1 or a pharmaceutically acceptable salt thereof to the mammal.

4. The bicyclo derivative according to claim 1, wherein the compound represented by the formula (1) is (2S,4S)-1-[[N-(4-carboxybicyclo[2,2,2]oct-1-yl)amino]acetyl]-4-fluropyrrolidine-2-carbonitrile or a pharmaceutically acceptable salt thereof.

* * * * *